United States Patent [19]

Bauer et al.

[11] Patent Number: 4,718,927
[45] Date of Patent: Jan. 12, 1988

[54] PROCESS FOR THE SEPARATION OF $C_{2+}$ HYDROCARBONS FROM NATURAL GAS

[75] Inventors: Heinz Bauer, Munich; Rainer Sapper, Neuried, both of Fed. Rep. of Germany

[73] Assignee: Linde Aktiengesellschaft, Wiesbaden, Fed. Rep. of Germany

[21] Appl. No.: 902,850

[22] Filed: Sep. 2, 1986

[30] Foreign Application Priority Data

Sep. 2, 1985 [DE] Fed. Rep. of Germany ....... 3531307

[51] Int. Cl.⁴ ................................................. F25J 3/00
[52] U.S. Cl. .......................................... 62/39; 62/24; 62/32
[58] Field of Search ................. 62/23, 24, 32, 38, 39, 62/42

[56] References Cited

U.S. PATENT DOCUMENTS

| | | | |
|---|---|---|---|
| 3,675,435 | 7/1972 | Jackson et al. | 62/23 X |
| 4,065,278 | 12/1977 | Newton et al. | 62/38 X |
| 4,140,504 | 2/1979 | Campbell et al. | 62/23 X |
| 4,203,741 | 5/1980 | Bellinger et al. | 62/23 X |
| 4,445,916 | 5/1984 | Newton | 62/38 X |
| 4,456,461 | 6/1984 | Perez | 62/39 X |
| 4,486,209 | 12/1984 | Fabbri et al. | 62/39 X |

*Primary Examiner*—Henry C. Yuen
*Assistant Examiner*—Steven E. Warner
*Attorney, Agent, or Firm*—Millen & White

[57] ABSTRACT

A process for the separation of $C_{2+}$ hydrocarbons from natural gas under pressure wherein the natural gas is cooled (2, 6), partially condensed, and separated (9) into a liquid fraction and a gaseous fraction. The liquid fraction (10) is subcooled (11) and then expanded into the upper zone of a rectifying column (7). The gaseous fraction (23), after engine expansion (25), is also introduced into the rectifying column (7). During rectification, a product stream (37) containing essentially $C_{2+}$ hydrocarbons and a residual gas stream (22) containing predominantly lower-boiling components are obtained. The residual gas stream (22) is initially heated by heat exchange (11) with the liquid fraction (10) and then heated by heat exchange (21) with the gaseous fraction obtained after partial condensation. The residual gas stream is then further heated (6, 2) by heat exchange with the feed stream of natural gas to be partially condensed. The heated residual gas is then engine expanded (28) and reheated again by heat exchange with the feed stream of natural gas to be partially condensed (2).

25 Claims, 1 Drawing Figure

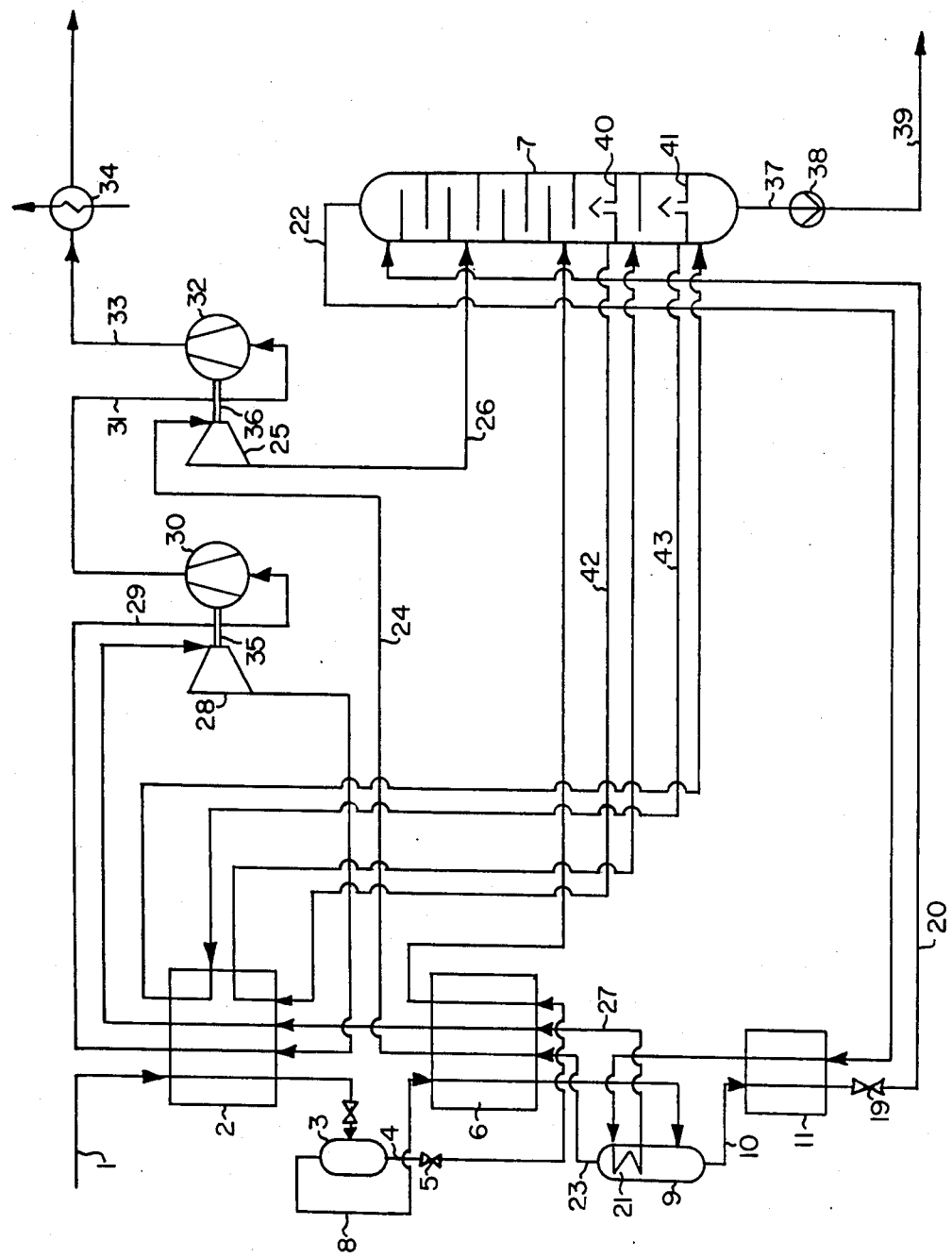

PROCESS FOR THE SEPARATION OF $C_{2+}$ HYDROCARBONS FROM NATURAL GAS

BACKGROUND OF THE INVENTION

This invention relates to a process for the separation of $C_{2+}$ hydrocarbons from a feed stream of natural gas under pressure, and in particular wherein the natural gas is cooled, partially condensed, and then separated into a liquid fraction and a gaseous fraction.

It is common for separated liquid fraction to be subcooled (i.e., cooled below the boiling point of its components) and then expanded into the upper zone of a rectifying column. It is also common for the gaseous fraction, after being expanded within a turbine or engine, to be introduced into the rectifying column. The rectification or fractionating process within the column produces a product stream containing essentially $C_{2+}$ hydrocarbons and a residual gas stream containing predominantly lower-boiling components, e.g., methane. It is also conventional, after being discharged from the rectifying column, for the residual gas to be reheated by heat exchange with the feed stream of natural gas.

In such an expansion method for $C_{2+}$ separation from natural gas, the low temperatures required for attaining a high yield of $C_{2+}$ hydrocarbons are produced by engine expansion of the gaseous fraction remaining after the partial condensation of the natural gas. During the expansion process, a large temperature difference occurs perforce between the inlet and outlet of the turbine or engine. The large temperature difference resulting from the cold-producing expansion is then effectively utilized in order to bring about an optimum increase in the yield of $C_{2+}$ gas.

U.S. Pat. No. 4,140,504 describes a process of the type discussed above wherein a portion of the gaseous fraction remaining after partial condensation is not work expanded for production of refrigeration. Instead, this portion of the gaseous fraction is combined with the liquid fraction which results in a reduction of the bubble point of the liquid fraction. The combined stream is then cooled and condensed by heat exchange with process streams and expanded by an expansion device. During expansion, a portion of the stream vaporizes and this further cools the remaining portion. The expanded stream is then supplied as top feed to the rectifying column. This process has the drawback that the amount of the gaseous fraction which is engine-expanded in the expansion turbine, as well as the total resultant work produced by expansion of the gaseous fraction, is diminished.

OBJECTS OF THE INVENTION

An object of one aspect of this invention is to provide a process for separation of $C_{2+}$ hydrocarbons from natural gas under pressure employing expansion of a gaseous fraction wherein a high yield of $C_{2+}$ is obtained.

An object of another aspect of this invention is to provide a process for separation of $C_{2+}$ hydrocarbons from natural gas which efficiently utilizes the cold temperatures produced by expansion of the gaseous fraction.

An object of still another aspect of the invention is to provide a process which improves the partial condensation of the natural gas feed stream.

An object of still another aspect of the invention is to provide an efficient system for performing the separation of $C_{2+}$ hydrocarbons from natural gas under pressure.

Upon further study of the specification and appended claims, further objects and advantages of this invention will become apparent to those skilled in the art.

SUMMARY OF THE INVENTION

The above objects are attained by providing a process and system wherein the residual gas stream, prior to heat exchange with the natural gas to be cooled and partially condensed, enters into heat exchange with the gaseous fraction obtained after the partial condensation and thereby provides an additional partial condensation. The components additionally condensed from the gaseous fraction during this step are then separated before the engine expansion of the gaseous fraction.

In contrast to the known process disclosed in U.S. Pat. No. 4,140,504, this invention eliminates remixing of a portion of the gaseous fraction with the liquid fraction. In this invention, condensation of the $C_{2+}$ hydrocarbons from the gaseous fraction is increased by an additional indirect heat exchange between the residual gas stream and the gaseous fraction. In this heat exchange, the temperature difference produced during engine expansion of the gaseous fraction is very effective because it is directly converted to produce additional liquid for the column reflux.

Due to the employment of this additional heat exchange a preliminary separation by rectification is performed, thus increasing the amount of $C_{2+}$ in the liquid feed to the rectifying column and/or lowering the quantity of $C_{1-}$ in the liquid feed, correspondingly.

In an advantageous further development of the process according to this invention, indirect heat exchange of the residual gas with the gaseous fraction is performed within a separator wherein the portion of the gaseous fraction that has been condensed during this additional heat exchange is separated from the fraction that has remained in the gaseous phase. The separator, in this case, is designed as a simple separation column with at least two equilibrium stages wherein the gaseous fraction of the partially condensed natural gas is fed into a lower zone of the column and indirect heat exchange between the residual gas and the gaseous fraction takes place in an upper zone of the column.

In comparing the invention to a conventional process, the invention differs by the provision of an additional heat exchanger positioned in the upper region of the separator at lower temperature.

The apparatus of the invention can be provided with either a single separator or two distinct separators. In the case where only one separator is employed the stream of partially condensed natural gas is fed to a lower zone of the separator and in the upper zone of the separator there is positioned an indirect heat exchanger for conducting heat exchange between the gas fraction of the partially condensed natural gas stream and the residual gas stream.

In contrast to the method disclosed in U.S. Pat. No. 4,140,504, there is no need for a distributing device for dividing the gaseous fraction delivered from the separator or for a two-phase feed means for a heat exchanger which cools the liquid fraction admixed with a portion of the gaseous fraction prior to their delivery to the rectifying column.

In another development of the process the liquid fraction discharged from the first separator, i.e., the separator receiving the partially condensed natural gas feed stream, is heated, rather than cooled. This first liquid fraction is heated by heat exchange with the gaseous fraction and then introduced into a middle zone of the rectifying column. This heating is done to remove the light components, e.g. $C_1$, which are already dissolved in the liquid before the stream enters the rectifying column in order to save energy. The second liquid fraction, i.e., the liquid fraction formed by the heat exchange between the gaseous fraction and the residual gas stream, undergoes heat exchange with the residual gas stream, is subcooled and after depressurization is fed to the rectifying column.

In a further development of the invention, the residual gas stream is heated against the liquid fraction to be subcooled before the residual gas stream undergoes heat exchange with the gaseous fraction and before the liquid fraction is delivered to the head of the rectifying column. By this further development, the residual gas stream leaving the head of the rectifying column at the lowest process temperature initially provides subcooling of the liquid fraction and thereafter is utilized for condensation of further $C_{2+}$ components from the gaseous fraction before entering into heat exchange with natural gas that is to be partially condensed. The temperature differences occurring on the cold end of the heat exchanger for partial condensation of the natural gas, and thus the refrigeration losses of the process, are thereby especially low.

In a further modification of the invention, the gaseous fraction, after having entered into heat exchange with the residual gas stream, is partially reheated by heat exchange with the feed stream of natural gas to be cooled before this fraction is engine expanded. After being expanded to the pressure of the rectifying column in the expansion engine, this fraction is then introduced into the rectifying column at a point lying below the feed point for the expanded, subcooled liquid fraction.

In another modification of the process according to this invention, the residual gas stream is heated to about the inlet temperature of the natural gas by the heat exchange with the feed stream of natural gas after the residual gas has already entered into heat exchange with the gaseous fraction. The residual gas is then engine expanded, to cover the refrigeration requirement of the initial partial condensation of the natural gas, and again heated, by heat exchange with the feed stream of natural gas, up to about the inlet temperature of the natural gas feed stream. After the engine-expanded residual gas has thus contributed toward covering the refrigeration requirement needed for initial partial condensation, it can be compressed, if needed, to an increased discharge pressure. For this purpose, the energy needed for compression can, for example, be obtained from the engine expansion of the residual gas stream itself and/or from the expansion of the gaseous fraction.

An installation for performing the process according to this invention comprises essentially at least one heat exchanger for initial cooling and partial condensation of the natural gas by heat exchange with process streams; a conventional separator for condensate separation; an expansion turbine for expansion of the gaseous fraction; a heat exchanger for subcooling the liquid fraction; a rectifying column for fractionating the gaseous and the subcooled liquid fractions and forming a residual gas stream and a product stream; and heat exchange means for indirect heat exchange between the gaseous fraction and the residual gas stream wherein additional components are condensed from the gaseous fraction. The heat exchange means for heat exchange between the gaseous fraction and the residual gas stream is preferably positioned within an upper zone of an additional separator wherein the additional separator includes a feed conduit which delivers the gaseous fraction into a lower zone of the additional separator. The heat exchanger of the additional separator is connected with a residual gas inlet conduit coming from the head of the rectifying column and with an outlet conduit which in turn is preferably connected to the heat exchanger utilized for the partial condensation of the natural gas.

BRIEF DESCRIPTION OF THE DRAWING

Additional details of the invention will be described below with reference to a preferred comprehensive embodiment illustrated schematically in the FIGURE.

DETAILED DESCRIPTION OF DRAWING

In the FIGURE, a natural gas stream containing 85.0% (percentages relating respectively to mol-%) of methane, 6.8% of ethane, 5.3% of $C_{3+}$ hydrocarbons, 2.7% of nitrogen, and 0.2% of carbon dioxide at a temperature of 300 K and a pressure of 70 bar is introduced via conduit 1 into a heat exchanger 2 where it is cooled to a temperature of 226 U and thereby subjected to a first partial condensation step. The partially condensed gas is fed under a pressure of 50 bar into a separator 3 to form a gaseous fraction and a liquid fraction. The liquid fraction or condensate is withdrawn via conduit 4, expanded to a pressure of 19 bar in valve 5, and, after being heated from 193 to 213 K in heat exchanger 6 by heat exchange with the gaseous fraction, is fed into the middle zone of a rectifying column 7. This liquid fraction contains 56.0% of methane, 17.9% of ethane, 25.3% of $C_{3+}$ hydrocarbons, and 0.6% of nitrogen and 0.2% of carbon dioxide. The gaseous phase, at a pressure of 50 bar and a temperature of 216 K, is withdrawn from separator 3 via conduit 8, cooled in heat exchanger 6 to 199 K, thus condensing additional components, and then fed into the lower zone of a second separator 9. The condensate or additional liquid fraction obtained in separator 9 contains 87.4% of methane, 8.0% of ethane, 2.5% of $C_{3+}$ hydrocarbons, 1.9% of nitrogen, and 0.2% of $CO_2$. This additional liquid fraction is introduced via conduit 10 into a heat exchanger 11 and subcooled to 167 K by heat exchange with the residual gas stream discharged from the head of the rectifying column 7. The additional liquid fraction is then expanded to 19 bar in valve 19 and introduced via conduit 20 as liquid feed to the head of rectifying column 7.

In the upper zone of separator 9, a heat exchanger 21 is provided. The residual gas stream withdrawn from the head of rectifying column 7 via conduit 22 is supplied to heat exchanger 21, after having been heated to as high as 185 K in heat exchanger 11 by heat exchange with the additional liquid fraction from separator 9. In heat exchanger 21 the residual gas stream is further heated to 197 K through heat exchange with the gaseous fraction in separator 9. The gaseous fraction from separator 9 is discharged via conduit 23, heated in heat exchanger 6 to 213 K, and then fed at a pressure of 50 bar via conduit 24 to an expansion turbine 25 and expanded in the latter to a pressure of 19 bar. During the expansion step, work is extracted and the gas fraction is cooled to 172 K before it is introduced into the rectifying column 7 via conduit 26. This gas fraction contains 93.4% of methane, 2.4% of ethane, 0.2% of $C_{3+}$ hydrocarbons, 3.9% of nitrogen, and 0.1% of carbon dioxide.

The rectifying column 7 is operated in a temperature range of between 166 K at the head and 281 K in the sump. The residual gas stream and the product stream are withdrawn from the head and the sump of the column, respectively, under a pressure of 18 bar. The residual gas or $C_1$-fraction withdrawn from the head via conduit 22 contains 96.4% of methane, 3.1% of nitrogen and only 0.5% of ethane. After the residual gas has been heated up to 197 K in heat exchangers 11 and 21 in the aforedescribed manner, it is delivered to heat exchanger 6 via conduit 27, where it is heated to 213 K. From heat exchanger 6 the residual gas is passed to heat exchanger 2 wherein it is heated to 262 K and thereafter delivered at a pressure of 17 bar to expansion turbine 28 wherein it is expanded, with consequent cooling, to a pressure of 9 bar and work is extracted. The cold residual gas is discharged from expansion turbine 28 at a pressure of 9 bar and a temperature of 229 K. This cold residual gas is subsequently reheated to 300 K in heat exchanger 2 by heat exchange with the natural gas feed stream, delivered to a compressor 30 via conduit 29. The residual gas stream is discharged from compressor 30 at a pressure of 11 bar and a temperature of 334 K and thereafter delivered to a further compressor 32 via conduit 31. The residual gas is discharged from compressor 32 under a pressure of about 12.4 bar as a methane product stream via conduit 33.

If desired, a heat exchanger 34 is provided for removal of the heat produced during compression. The compressors 30 and 32 are driven by way of shafts 35 and 36, respectively, connected to expansion turbines 28 and 25, respectively, so that no additional energy is required for the recompression of the methane-rich $C_{1-}$ gas.

In the sump of the rectifying column 7, a $C_{2+}$ fraction containing 53.4% of ethane, 44.6% of $C_{3+}$ hydrocarbons and only 1.0% of methane and 1.0% of carbon dioxide is withdrawn by way of conduit 37. This stream contains about 96.5% of the $C_{2+}$ hydrocarbons introduced via conduit 1 into the fractionation process. The product stream is pumped by means of pump 38 to an elevated pressure of 30 bar and then fed to a consumer via conduit 39.

In the lower zone of the rectifying column 7, two chimney plates 40, 41 are disposed. Above the plates 40, 41, liquid is discharged via conduits 42 and 43, respectively, and heated in heat exchanger 2. The liquid in conduit 42 withdrawn from the higher chimney plate 40 is conducted through the colder portion of heat exchanger 2 whereas the liquid withdrawn via conduit 43 from the lower-level chimney plate 41 is passed through the warmer portion of heat exchanger 2. Depending on the feedgas quantity, the heat exchangers 2 and 6 are divided into two or more blocks arranged in parallel or in series. If heat exchanger 2 consists of two blocks in series, for example, stream 42 is routed to the block with the lower temperature and stream 43 to the block with the higher temperature. The heated-up liquids are respectively reintroduced into the rectifying column 7 below their associated chimney plate. Thereby, the required intermediate heating and heat for the bottom reboiler of the column 7 is coupled with the supply of cold for the heat exchanger 2.

With the exception of heat exchanger 34, no external cold is required for performing the previously described process. The cold for heat exchanger 34 can be provided by water or ambient air.

The preceding example can be repeated with similar success by substituting the generically or specifically described reactants and/or operating conditions of this invention for those used in the preceding example.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for the separation of $C_{2+}$ hydrocarbons from a feed stream of natural gas under pressure, wherein
   (a) said feed stream is cooled to partially condense said natural gas thereby forming a liquid fraction and a gaseous fraction;
   (b) said liquid fraction and said gaseous fraction are separated;
   (c) said liquid fraction is delivered to a rectifying column wherein there is produced a product stream consisting essentially of $C_{2+}$ hydrocarbons and a residual gas stream comprising lower-boiling components;
   (d) said gaseous fraction is delivered to an expansion engine wherein said gaseous fraction is expanded and work is extracted therefrom, said gaseous fraction is then supplied to said rectifying column; and
   (e) said residual gas stream is discharged from said rectifying column and is heated by heat exchange with said feed stream in step (a),
   the improvement comprising subjecting said residual gas stream, prior to the heat exchange in step (e), to heat exchange with said gaseous fraction, prior to delivery of said gaseous fraction to said expansion engine, wherein said gaseous fraction is partially condensed to form an additional liquid fraction; separating said additional liquid fraction from said gaseous fraction, prior to delivery of said gaseous fraction to said expansion engine, wherein step (b) and the latter separation of said additional liquid fraction from said gaseous fraction are performed at substantially the same pressure; and delivering said additional liquid fraction to said rectifying column.

2. A process according to claim 1, wherein the residual gas stream, prior to its heat exchange with the gaseous fraction, is heated by heat exchange with said additional liquid fraction prior to delivery of said additional liquid fraction to said rectifying column.

3. A process according to claim 1, wherein the gaseous fraction, prior to its delivery to said expansion engine, is heated by heat exchange with said feed stream.

4. A process according to claim 1, wherein said liquid fraction is introduced into a middle zone of said rectifying column, said additional liquid fraction is introduced into an upper zone of said rectifying column, and said gaseous fraction is introduced into said rectifying column at a point below that at which said additional liquid fraction is introduced.

5. A process according to claim 1, wherein no external refrigeration is required.

6. A process according to claim 1, wherein separation step (b), heat exchange between the residual gas stream and the gaseous fraction, and the separation of the additional liquid fraction from the gaseous fraction are all performed in a single separation column.

7. The process according to claim 1, wherein said liquid fraction, prior to its delivery to said rectifying column, is heated by heat exchange with said gaseous fraction and then introduced into a middle zone of said rectifying column.

8. A process according to claim 1, wherein the product stream contains about 96.5% of the $C_{2+}$ hydrocarbons introduced by the feed stream.

9. A process according to claim 8, wherein no external refrigeration is required.

10. A process according to claim 1, wherein in the heat exchange between the residual gas stream and the gaseous fraction and the separation of the additional liquid fraction from the gaseous fraction are performed within a separation colum having at least two equilibrium stages, said gaseous fraction being fed into a lower zone of said separation column, and the heat exchange between the residual gas stream and the gaseous fraction being conducted within an upper zone of said separation column.

11. A process according to claim 10, wherein separation step (b), heat exchange between the residual gas stream and the gaseous fraction, and the separation of the additional liquid fraction from the gaseous fraction are all performed in a single separation column.

12. The process according to claim 10, wherein said heat exchange between the residual gas stream and the gaseous fraction is indirect heat exchange.

13. A process according to claim 1, wherein in step (e) the residual gas stream is heated to about the inlet temperature of said feed stream.

14. A process according to claim 13, wherein, after being heated by heat exchange with the feed stream, the residual gas stream is expanded in an expansion engine, from which work is extracted, and then reheated by heat exchange with the feed stream up to about the inlet temperature of said feed stream.

15. A process according to claim 14, wherein, after being subjected to engine expansion and reheated by heat exchange with the feed stream, the residual gas stream is compressed by means utilizing the work extracted during engine expansion of the gaseous fraction in step (d).

16. A process according to claim 14, wherein, after being subjected to engine expansion and reheated by heat exchange with the feed stream, the residual gas stream is compressed by means utilizing the work extracted during engine expansion of the residual gas.

17. A process according to claim 16, wherein the residual gas stream is further compressed by means utilizing the work extracted during engine expansion of the gaseous fraction in step (d).

18. In an apparatus for performing a process for the separation of $C_{2+}$ hydrocarbons from a feed stream of natural gas under pressure comprising:
at least one first indirect head exchanger for cooling and partial condensation of a natural gas feed stream to form a first liquid fraction and a gaseous fraction;
a first separator for separating said first liquid fraction from said gaseous fraction;
an expansion engine for expansion of said gaseous fraction; and
a rectifying column for fractionating said first liquid fraction and said gaseous fraction, said rectifying column having a residual gas stream discharge conduit and a product stream discharge conduit,
wherein the improvement comprises a second separator having a feed conduit which delivers said gaseous fraction from said first separator to a lower zone of said second separator and a second indirect heat exchanger positioned in an upper zone of said second separator, said second indirect heat exchanger having an inlet connected to said residual gas stream discharge conduit and a corresponding outlet connected to an outlet conduit, said outlet conduit being connected to said at least one first indirect heat exchanger for cooling and partial condensation of said natural gas feed stream.

19. An apparatus according to claim 18, wherein said second separator has at least two equilibrium stages.

20. In an apparatus for performing a process for the separation of $C_{2+}$ hydrocarbons from a feed stream of natural gas under pressure comprising:
at least one first indirect heat exchanger for cooling and partial condensation of a natural gas feed stream to form a liquid fraction and a gaseous fraction;
a separator for separating said liquid fraction from said gaseous fraction;
an expansion turbine for expansion of said gaseous fraction;
a second indirect heat exchanger for subcooling the liquid fraction; and
a rectifying column for fractionating the gaseous fraction and the subcooled liquid fraction, said rectifying column having a residual gas stream discharge conduit and a product stream discharge conduit,
wherein the improvement comprises said separator having a feed conduit from said at least one indirect heat exchanger for delivering partially condensed natural gas to a lower zone of said separator and a third indirect heat exchanger in an upper zone of said separator, said third indirect heat exchanger having an inlet connected to said residual gas stream discharge conduit and a corresponding outlet connected to an outlet conduit, said outlet conduit being connected to said at least one first indirect heat exchanger for cooling and partial condensation of said natural gas feed stream.

21. An apparatus according to claim 20, wherein said separator has at least two equilibrium stages.

22. In a process for the separation of $C_{2+}$ hydrocarbons from a feed stream of natural gas under pressure, wherein
(a) said feed stream is cooled to partially condense said natural gas thereby forming a liquid fraction and a gaseous fraction;
(b) said liquid fraction and said gaseous fraction are separated;
(c) said liquid fraction is delivered to a rectifying column wherein there is produced a product stream consisting essentially of $C_{2+}$ hydrocarbons and a residual gas stream comprising lower-boiling components;
(d) said gaseous fraction is delivered to an expansion engine wherein said gaseous fraction is expanded and work is extracted therefrom, said gaseous fraction is then supplied to said rectifying column; and
(e) said residual gas stream is discharged from said rectifying column and is heated by heat exchange with said feed stream in step (a), the improvement comprising subjecting said residual gas stream, prior to the heat exchange in step (e), to heat exchange with said gaseous fraction, prior to delivery of said gaseous fraction to said expansion engine, wherein said gaseous fraction is partially condensed to form an additional liquid fraction; separating said additional liquid fraction from said gaseous fraction, prior to delivery of said gaseous fraction to said expansion engine; and delivering said additional liquid fraction to said rectifying column, wherein the heat exchange between said residual gas stream and said gaseous fraction and the separation of said additional liquid fraction from said gaseous fraction are both performed within a separation column having at least two equilibrium stages, said gaseous fraction being fed into a lower zone of said separation column, and the heat exchange between said residual gas stream and said gaseous fraction being conducted within an upper zone of said separation column.

23. In a process for the separation of $C_{2+}$ hydrocarbons from a feed stream of natural gas under pressure, wherein
   (a) said feed stream is cooled to partially condense said natural gas thereby forming a liquid fraction and a gaseous fraction;
   (b) said liquid fraction and said gaseous fraction are separated;
   (c) said liquid fraction is delivered to a rectifying column wherein there is produced a product stream consisting essentially of $C_{2+}$ hydrocarbons and a residual gas stream comprising lower-boiling components;
   (d) said gaseous fraction is delivered to an expansion engine wherein said gaseous fraction is expanded and work is extracted therefrom, said gaseous fraction is then supplied to said rectifying column; and
   (e) said residual gas stream is discharged from said rectifying column and is heated by heat exchange with said feed stream in step (a),
the improvement comprising subjecting said residual gas stream, prior to the heat exchange in step (e), to heat exchange with said gaseous fraction, prior to delivery of said gaseous fraction to said expansion engine, wherein said gaseous fraction is partially condensed to form an additional liquid fraction; separating said additional liquid fraction from said gaseous fraction, prior to delivery of said gaseous fraction to said expansion engine; and delivering said additional liquid fraction to said rectifying column, wherein said residual gas stream, prior to its heat exchange with said gaseous fraction, is heated by heat exchange with said additional liquid fraction.

24. In a process for the separation of $C_{2+}$ hydrocarbons from a feed stream of natural gas under pressure, wherein
   (a) said feed stream is cooled to partially condense said natural gas thereby forming a liquid fraction and a gaseous fraction;
   (b) said liquid fraction and said gaseous fraction are separated;
   (c) said liquid fraction is delivered to a rectifying column wherein there is produced a product stream consisting essentially of $C_{2+}$ hydrocarbons and a residual gas stream comprising lower-boiling components;
   (d) said gaseous fraction is delivered to an expansion engine wherein said gaseous fraction is expanded and work is extracted therefrom, said gaseous fraction is then supplied to said rectifying column; and
   (e) said residual gas stream is discharged from said rectifying column and is heated by heat exchange with said feed stream in step (a),
the improvement comprising subjecting said residual gas stream, prior to the heat exchange in step (e), to heat exchange with said gaseous fraction prior to delivery of said gaseous fraction to said expansion engine, wherein said gaseous fraction is partially condensed to form an additional liquid fraction; separating said additional liquid fraction from said gaseous fraction, prior to delivery to said gaseous fraction to said expansion engine, and delivering said additional liquid fraction to said rectifying column; heating said residual gas stream is step (e) to about the inlet temperature of said feed stream and subsequently expanding said residual gas stream in an expansion engine from which work is extracted; and reheating said residual gas stream to the inlet temperature of said feed stream by heat exchange with said feed stream.

25. In a process for the separation of $C_{2+}$ hydrocarbons from a feed stream of natural gas under pressure, wherein
   (a) said feed stream is cooled to partially condense said natural gas thereby forming a liquid fraction and a gaseous fraction;
   (b) said liquid fraction and said gaseous fraction are separated;
   (c) said liquid fraction is delivered to a rectifying column wherein there is produced a product stream consisting essentially of $C_{2+}$ hydrocarbons and a residual gas stream comprising lower-boiling components;
   (d) said gaseous fraction is delivered to an expansion engine wherein said gaseous fraction is expanded and work is extracted therefrom, said gaseous fraction is then supplied to said rectifying column; and
   (e) said residual gas stream is discharged from said rectifying column and is heated by heat exchange with said feed stream in step (a),
the improvement comprising subjecting said residual gas stream, prior to the heat exchange in step (e), to heat exchange with said gaseous fraction, prior to delivery of said gaseous fraction to said expansion engine, wherein said gaseous fraction is partially condensed to form an additional liquid fraction; separating said additional liquid fraction from said gaseous fraction, prior to delivery of said gaseous fraction to said expansion engine; and delivering said additional liquid fraction to said rectifying column, wherein separation step (b), said heat exchange between said residual gas stream and said gaseous fraction, and the separation of said additional liquid fraction from said gaseous fraction are all performed in a single separation column.

* * * * *